United States Patent [19]

Nakagawa et al.

[11] Patent Number: 5,478,567
[45] Date of Patent: Dec. 26, 1995

[54] ANTIPHLOGISTIC ANALGESIC PLASTER

[75] Inventors: Akira Nakagawa; Munehiko Hirano; Tetsuro Tateishi, all of Tosu, Japan

[73] Assignee: Hisamitsu Pharmaceutical Co., Inc., Saga, Japan

[21] Appl. No.: 199,223

[22] PCT Filed: Aug. 10, 1992

[86] PCT No.: PCT/JP92/01022

§ 371 Date: Mar. 21, 1998

§ 102(e) Date: Mar. 21, 1994

[87] PCT Pub. No.: WO93/04677

PCT Pub. Date: Mar. 18, 1993

[51] Int. Cl.⁶ .......................... A61F 13/02; A61L 15/24; A61L 15/58; A61L 15/42

[52] U.S. Cl. .......................... 424/449; 424/485; 424/486; 424/448; 602/48; 602/54; 428/355

[58] Field of Search .................. 514/772.4, 782, 514/783; 424/485, 486, 443, 448, 449; 524/78

[56] References Cited

U.S. PATENT DOCUMENTS

| | | | |
|---|---|---|---|
| 4,455,146 | 6/1984 | Noda et al. | 424/447 |
| 4,661,104 | 4/1987 | von Bittera et al. | 424/449 |
| 4,814,168 | 3/1989 | Sablotsky et al. | 424/449 |
| 5,296,235 | 3/1994 | Sawayanagi et al. | 424/445 |

*Primary Examiner*—Edward J. Webman
*Attorney, Agent, or Firm*—Bucknam and Archer

[57] ABSTRACT

An antiphlogistic analgesic plaster which comprises as essential ingredients:

(a) at least one nonsteroidal antiphlogistic analgesic drug selected from among ketoprofen, flurbiprofen, loxoprofen, ketorolac and ester derivatives or salts thereof, (b) a solubilizer comprising a combination of a rosin ester derivative with l-menthol, (e) a styrene/isoprene/styrene block copolymer employed as a base polymer, (d) a softener, and (e) a backing comprising a polyester cloth.

5 Claims, 1 Drawing Sheet

○ : Ex. 4
□ : Ex. 8
△ : Ex. 10
☆ : Ex. 17
● : Ref. Ex. 1
■ : Ref. Ex. 2
▲ : Ref. Ex. 3
★ : Ref. Ex. 4

ANTIPHLOGISTIC ANALGESIC PLASTER

TECHNICAL FIELD

This invention relates to a novel antiphlogistic analgesic plaster for therapeutic use which contains at least one nonsteroidal antiphlogistic analgesic drug selected from among ketoprofen, flurbiprofen, loxoprofen, ketorolac and esters or salts thereof and a rosin ester derivative and l-menthol employed as a solvent and has a polyester cloth employed as a backing.

BACKGROUND ART

Attempts have been widely made to apply so-called tapes comprising a nonsteroidal antiphlogistic (or anti-inflammatory) analgesic drug contained in an oily pressure-sensitive adhesive to therapeutic uses. For example, Japanese Patent Laid-Open Gazette No. 227819/1984 has disclosed an attempt to administer a nonsteroidal antiphlogistic analgesic drug which is contained in an acrylic pressure-sensitive adhesive located on a composite backing consisting of a nonwoven fabric and a film. Further, Japanese Patent Laid-Open Gazette No. 139615/1985 has disclosed an attempt to administer ketoprofen which is contained in a pressure-sensitive adhesive comprising polyisobutylene/paraffin/rosin-modified glycerol ester, to allow the ketoprofen to be percutaneously absorbed. Japanese Patent Laid-Open Gazette No. 227524/1988 has disclosed an attempt to administer flurbiprofen together with an oily base. Furthermore, Japanese Patent Laid-Open No. 40420/1989 has disclosed an attempt to administer, together with an oily base, a nonsteroidal antiphlogistic analgesic drug having a carboxyl group.

However, none of these attempts are satisfactory in drug-release characteristics or percutaneous absorption characteristics. It is therefore urgently required to develop a preparation having superior properties.

It is an object of the present invention to provide an antiphlogistic analgesic plaster having characteristics remarkably improved in the following points:

(1) improvement in percutaneous absorption (improvements in the solubility and releasability of a nonsteroidal antiphlogistic analgesic drug in a base), (2) improvement in drug-releasability (selection of a backing not adsorbing a nonsteroidal antiphlogistic analgesic drug), (3) relief from side effects including skin rash caused by repeated plastering (utilization of a safe base and search for not adhesion but stickiness through the establishment of an appropriate compositional ratio of the base), and (4) convenient usability in the remedial field (impartment of such stretchability as to enable the stickiness to a flexional part).

SUMMARY OF THE INVENTION

In order to achieve the above-mentioned object, the present inventors have conducted extensive studies on ketoprofen, flurbiprofen, loxoprofen and ketorolac, which are nonsteroidal antiphlogistic analgesic drugs having carboxylic acid, and ester derivatives or salts thereof. As a result of their studies, they have successfully completed the development of an antiphlogistic analgesic plaster according to the present invention which is characterized by comprising the following ingredients (a) to (e) as essential ingredients.

Accordingly, the antiphlogistic analgesic plaster of this invention comprises as essential ingredients:

(a) at least one nonsteroidal antiphlogistic analgesic drug selected from among ketoprofen, flurbiprofen, loxoprofen, ketorolac and ester derivatives or salts thereof;

(b) a solubilizer comprising a combination of a rosin ester derivative with l-menthol;

(c) a styrene/isoprene/styrene block copolymer employed as a base polymer;

(d) a softener; and (e) a backing comprising a polyester cloth.

As the backing to be used in the present invention, polyester cloths exerting no effect on the release of the nonsteroidal antiphlogistic analgesic drug are selected. Among others, a cloth made from PET (polyethylene terephthalate) or PBT (polybutylene terephthalate) is preferable. In order to achieve excellent release of the nonsteroidal antiphlogistic analgesic drug, it is essentially required that the backing undergoes no interaction with the nonsteroidal antiphlogistic analgesic drug, namely, never adsorbs the drug. As the result of the examination of backings of various compositions, the present inventors have found out that PET and PBT are the most suitable polymer composition for the backing. By using a backing comprising PET or PBT, excellent release can be achieved without causing any adsorption of the drug on the backing.

The antiphlogistic analgesic plaster of the present invention is endowed with such a stretchability having an average stress of 0.3 kg/cm or below when it is 50% elongated in the longitudinal or lateral direction as to enable the antiphlogistic analgesic plaster to be applied even to a flexional part. This stretchability makes it possible not only to conveniently use the antiphlogistic analgesic plaster of the present invention but also to reduce the friction and oppression at the time of application of the plaster owing to the fact that the plaster follows the movement of the skin to thereby reduce a side effect (a skin rash).

The present invention is particularly characterized by finding that when compounded with l-menthol in a specified ratio, a rosin ester derivative which has been known as a tackiness-providing resin to those skilled in the art, will serve as a solubilizer for the nonsteroidal antiphlogistic analgesic drug. It has been further found that the rosin ester derivative so compounded will greatly improve the release of the nonsteroidal antiphlogistic analgesic drug. In order to satisfactorily dissolve the nonsteroidal antiphlogistic analgesic drug and release the same, it is preferable that the nonsteroidal antiphlogistic analgesic drug, rosin ester derivative and l-menthol be mixed together in ratio by weight of 1.0:3.0–11.0:1.0–4.0. Within the range of said ratios, the nonsteroidal antiphlogistic analgesic drug will exhibit satisfactory solubility and releasability.

The rosin ester derivative as used herein refers to those obtained by esterifying various rosins followed by the hydrogenation or purification of the same so esterified. Depending on the type of the ester, methyl esters, glycerol esters, pentaerythritol esters, and the like may be cited. Particular examples thereof include Ester Gums A, AA-G, H and HP (tradenames, mfd. by Arakawa Kagaku K.K.), Hariesters L, S and P (tradenames, mfd. by Harima Chemicals, Inc.), Superester A-75 (tradename, mfd. by Arakawa Kagaku, K.K.), KE-311 (tradename, mfd. by Arakawa Kagaku K.K.), Hercolyn D (tradename, mfd. by Hercules) and Forals 85 and 105 (tradenames, mfd. by Hercules).

Next, the base polymer of the present invention may be appropriately selected from among known ones in view of its safety for the skin, drug-releasability and stickiness to the skin. In view of the releasability of the nonsteroidal antiphlogistic analgesic drug, it is particularly preferable to use a styrene/isoprene/styrene block copolymer having low polarity as the base polymer. Particular examples of said block copolymer include Carlflexes TR-1107, TR-1111, TR-1112 and TR-1117 (tradenames, mfd. by Shell Chemical) and Solprene 428 (tradename, mfd. by Phillips Petroleum). A styrene/isoprene/styrene block copolymer is used in the present invention as a base polymer as described above, and, furthermore, other polymers such as polyisobutylene may be used together with it.

A softener is a substance which plasticizes and softens the styrene/isoprene/styrene block copolymer employed as a base polymer to thereby contribute to the maintenance of a suitable stickiness of the block copolymer to the skin. The softener includes almond oil, olive oil, camellia oil, persic oil, peanut oil, olefinic acids or liquid paraffin. The softener is preferably used in a mixing ratio of from 150 to 350 parts by weight per 100 parts by weight of the styrene/isoprene/styrene block copolymer.

Although the content of the nonsteroidal antiphlogistic analgesic drug in the plaster is not particularly restricted, it preferably ranges from 100 to 430 µg/cm$^2$ from the viewpoint of the release and usability of the drug in such an amount as to effectively contribute to the treatment and the bioavailability.

In the plaster preparation as a whole, the nonsteroidal antiphlogistic analgesic drug, the rosin ester derivative, l-menthol, the styrene/isoprene/styrene block copolymer and the softener may be preferably used each in such an amount as specified below:

| | |
|---|---|
| nonsteroidal antiphlogistic analgesic drug | 0.5–10.0% by weight |
| rosin ester derivative | 5.0–70.0% by weight |
| l-menthol | 0.5–15.0% by weight |
| styrene/isoprene/styrene block copolymer | 5.0–40.0% by weight |
| softener | 10.0–75.0% by weight |

It is needless to say that the antiphlogistic analgesic plaster according to the present invention may contain additional ingredients such as inorganic fillers, antioxidants, UV absorbers, antihistamines, antibacterial agents and perfumes which have been publicly known in the art without any restriction, if required.

The antiphlogistic analgesic plaster of the present invention can be easily produced by a conventional method. For example, the styrene/isoprene/styrene block copolymer is heated and mixed with the softener and with the rosin ester derivative in a mixing device such as a kneader or a mixer at a temperature of 120° to 160° C. to obtain a mixture. Then the nonsteroidal antiphlogistic analgesic drug and l-menthol are added to the mixture and mixed to obtain a preparation. Next, the obtained preparation is directly applied onto a polyester cloth or a nonwoven fabric. Alternatively, the preparation is temporarily spread on a paper or film previously subjected to a mold-release treatment, covered with a desired backing and then pressed to effect the transfer of the spread preparation onto the backing.

As will be described in the Examples and Test Examples hereinafter, the antiphlogistic analgesic plaster of the present invention thus obtained is surely an ideal one having the following properties and being highly useful in the industrial field:

(1) improved percutaneous absorptivity, (2) improved drug-releasability, (3) reduction in side effects including skin rash caused by repeated plastering, and (4) convenient use in the field of remedy (impartment of such a stretchability as to enable the plaster to stick to a flexional part).

Figure 1:
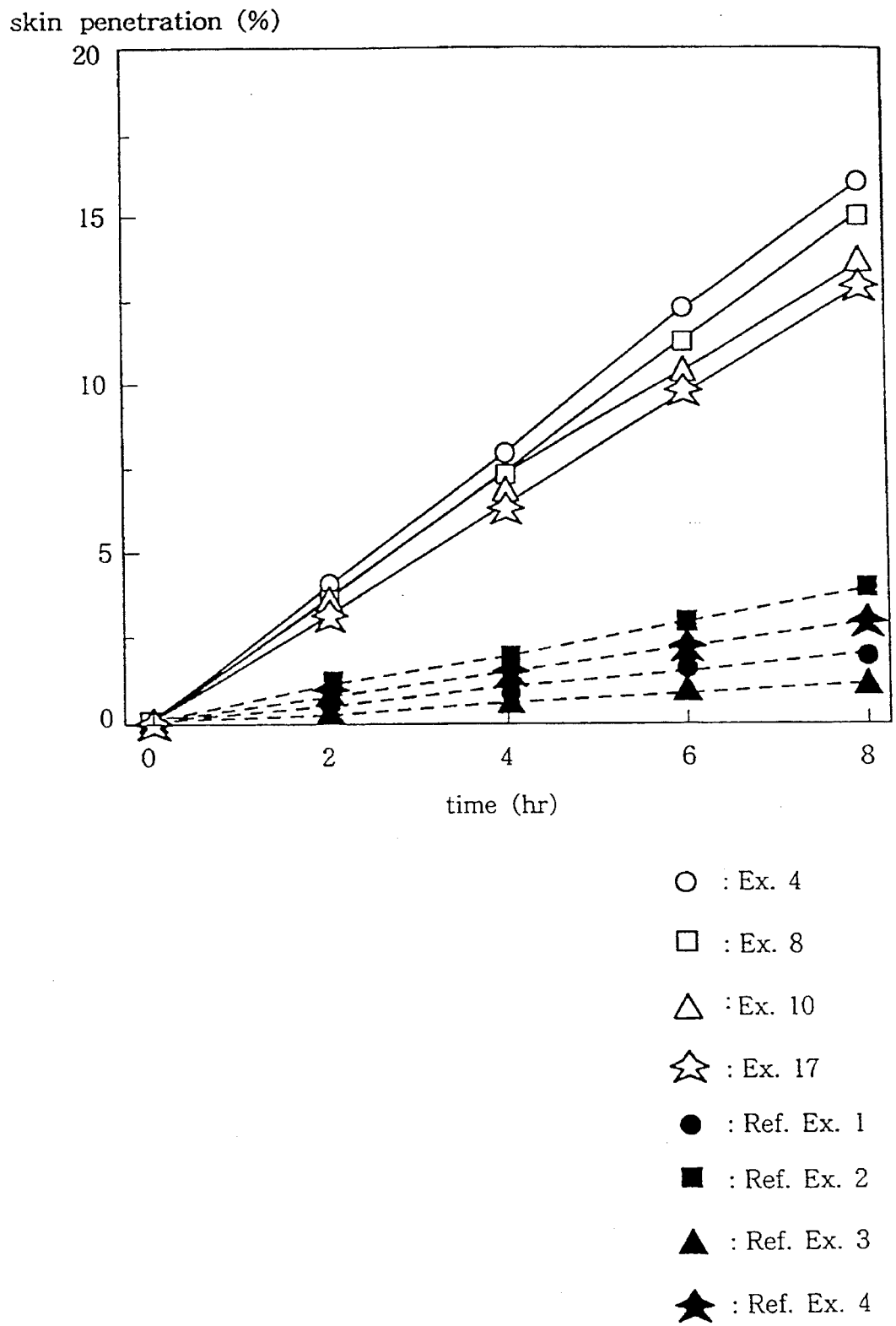
FIG. 1 is a graph which shows the results of a skin penetration test on hairless mice.

To further illustrate the present invention in greater detail, the following Examples, Test Examples and the like will be given. In these Examples, Comparative Examples and Referential Examples, all parts are by weight unless otherwise specified.

EXAMPLE 1

| | |
|---|---|
| styrene/isoprene/styrene block copolymer (tradename: Cariflex TR-1107) | 25.0 parts |
| liquid paraffin | 68.0 parts |
| rosin ester derivative (tradename: Ester Gum AA-G) | 5.0 parts |
| l-menthol | 1.5 parts |
| ketoprofen | 0.5 parts |

In accordance with this formulation, a plaster was produced by the above-mentioned method. Namely, the styrene/isoprene/styrene block copolymer was heated and mixed with the softener and the rosin ester derivative in a kneader employed as a mixing device at a temperature of 120° to 160° C. to obtain a mixture. Subsequently, the nonsteroidal antiphlogistic analgesic drug (ketoprofen) and l-menthol were added to the thus obtained mixture and mixed to obtain a preparation. The obtained preparation was spread directly on a polyester cloth (PET) and then cut into pieces of a desired size.

EXAMPLE 2

| | |
|---|---|
| styrene/isoprene/styrene block copolymer (tradename: Cariflex TR-1107) | 20.0 parts |
| liquid paraffin | 43.5 parts |
| butylhydroxytoluene | 2.0 parts |
| rosin ester derivative (tradename: KE-311) | 28.5 parts |
| l-menthol | 3.0 parts |
| ketoprofen | 3.0 parts |

In accordance with this formulation, a plaster was produced by the same method as described in the above Example 1.

EXAMPLE 3

| | |
|---|---|
| styrene/isoprene/styrene block copolymer (tradename: Cariflex TR-1107) | 21.0 parts |
| liquid paraffin | 63.0 parts |
| butylhydroxytoluene | 2.0 parts |
| rosin ester derivative (tradename: KE-311) | 8.0 parts |
| l-menthol | 4.0 parts |
| ketoprofen | 2.0 parts |

In accordance with this formulation, a plaster was produced by the same method as described in the above Example 1.

EXAMPLE 4

| | |
|---|---|
| styrene/isoprene/styrene block copolymer (tradename: Cariflex TR-1111) | 30.0 parts |
| liquid paraffin | 57.0 parts |
| butylhydroxytoluene | 2.0 parts |
| rosin ester derivative (tradename: Ester Gum H) | 7.0 parts |
| l-menthol | 3.0 parts |
| ketoprofen | 1.0 part. |

In accordance with this formulation, a plaster was produced by the same method as described in the above Example 1.

EXAMPLE 5

| | |
|---|---|
| Styrene/isoprene/styrene block copolymer (tradename: Cariflex TR-1111) | 15.0 parts |
| polyisobutylene (mfd. by Exxon Co.) | 5.0 parts |
| liquid paraffin | 23.0 parts |
| butylhydroxytoluene | 2.0 parts |
| rosin ester derivative (tradename: Ester Gum H) | 40.0 parts |
| l-menthol | 10.0 parts |
| ketoprofen | 5.0 parts. |

In accordance with this formulation, a plaster was produced by the same method as described in the above Example 1.

EXAMPLE 6

| | |
|---|---|
| Styrene/isoprene/styrene block copolymer (tradename: Cariflex TR-1112) | 18.0 parts |
| liquid paraffin | 54.5 parts |
| butylhydroxytoluene | 2.0 parts |
| rosin ester derivative (tradename: Foral 105) | 16.5 parts |
| l-menthol | 6.0 parts |
| ketoprofen ethyl ester | 3.0 parts. |

In accordance with this formulation, a plaster was produced by the same method as described in the above Example 1.

EXAMPLE 7

| | |
|---|---|
| Styrene/isoprene/styrene block copolymer (tradename: Solprene 418) | 28.0 parts |
| polybutene | 5.0 parts |
| liquid paraffin | 57.7 parts |
| butylhydroxytoluene | 2.0 parts |
| rosin ester derivative (tradename: KE-311) | 5.0 parts |
| l-menthol | 1.8 parts |
| flurbiprofen | 0.5 parts. |

EXAMPLE 8

| | |
|---|---|
| Styrene/isoprene/styrene block copolymer (tradename: Cariflex TR-1107) | 21.0 parts |
| liquid paraffin | 66.8 parts |
| butylhydroxytoluene | 2.0 parts |
| rosin ester derivative (tradename: KE-311) | 8.0 parts |
| l-menthol | 1.2 parts |
| flurbiprofen | 1.0 part. |

In accordance with this formulation, a plaster was produced by the same method as described in the above Example 1.

EXAMPLE 9

| | |
|---|---|
| Styrene/isoprene/styrene block copolymer (tradename: Cariflex TR-1107) | 11.0 parts |
| Styrene/isoprene/styrene block copolymer (tradename: Cariflex TR-1111) | 11.0 parts |
| liquid paraffin | 44.0 parts |
| butylhydroxytoluene | 2.0 parts |
| rosin ester derivative (tradename: Ester Gum AA-G) | 20.0 parts |
| l-menthol | 7.0 parts |
| flurbiprofen | 5.0 parts. |

In accordance with this formulation, a plaster was produced by the same method as described in the above Example 1.

EXAMPLE 10

| | |
|---|---|
| Styrene/isoprene/styrene block copolymer (tradename: Cariflex TR-1107) | 30.0 parts |
| liquid paraffin | 56.0 parts |
| butylhydroxytoluene | 2.0 parts |
| rosin ester derivative (tradename: KE-311) | 8.0 parts |
| l-menthol | 3.0 parts |
| loxoprofen | 1.0 part. |

In accordance with this formulation, a plaster was produced by the same method as described in the above Example 1.

EXAMPLE 11

| | |
|---|---|
| Styrene/isoprene/styrene block copolymer (tradename: Cariflex TR-1111) | 12.0 parts |
| liquid paraffin | 26.0 parts |
| butylhydroxytoluene | 2.0 parts |
| rosin ester derivative (tradename: Ester Gum H) | 40.0 parts |
| l-menthol | 12.0 parts |
| loxoprofen | 8.0 parts. |

In accordance with this formulation, a plaster was produced by the same method as described in the above Example 1.

EXAMPLE 12

| | |
|---|---|
| Styrene/isoprene/styrene block copolymer (tradename: Cariflex TR-1112) | 21.0 parts |
| liquid paraffin | 50.0 parts |
| butylhydroxytoluene | 2.0 parts |
| rosin ester derivative (tradename: Ester Gum H) | 20.5 parts |
| l-menthol | 3.5 parts |
| loxoprofen | 3.0 parts. |

In accordance with this formulation, a plaster was produced by the same method as described in the above Example 1.

EXAMPLE 13

| | |
|---|---|
| Styrene/isoprene/styrene block copolymer (tradename: Cariflex TR-1111) | 5.0 parts |
| liquid paraffin | 11.0 parts |
| butylhydroxytoluene | 2.0 parts |
| rosin ester derivative (tradename: KE-311) | 65.0 parts |
| l-menthol | 10.0 parts |
| loxoprofen sodium | 7.0 parts. |

In accordance with this formulation, a plaster was produced by the same method as described in the above Example 1.

EXAMPLE 14

| | |
|---|---|
| Styrene/isoprene/styrene block copolymer (tradename: Cariflex TR-1107) | 20.0 parts |
| liquid paraffin | 45.0 parts |
| butylhydroxytoluene | 2.0 parts |
| rosin ester derivative (tradename: Ester Gum H) | 21.0 parts |
| l-menthol | 9.0 parts |
| loxoprofen sodium | 3.0 parts. |

In accordance with this formulation, a plaster was produced by the same method as described in the above Example 1.

EXAMPLE 15

| | |
|---|---|
| Styrene/isoprene/styrene block copolymer (tradename: Cariflex TR-1107) | 22.0 parts |
| polyisobutylene (mfd. by Exxon Co.) | 5.0 parts |
| liquid paraffin | 52.0 parts |
| butylhydroxytoluene | 2.0 parts |
| rosin ester derivative (tradename: Hercolyn D) | 10.0 parts |
| l-menthol | 7.0 parts |
| loxoprofen | 2.0 parts. |

In accordance with this formulation, a plaster was produced by the same method as described in the above Example 1.

EXAMPLE 16

| | |
|---|---|
| Styrene/isoprene/styrene block copolymer (tradename: Cariflex TR-1107) | 20.0 parts |
| liquid paraffin | 38.0 parts |
| butylhydroxytoluene | 2.0 parts |
| rosin ester derivative (tradename: KE-311) | 28.0 parts |
| l-menthol | 8.0 parts |
| ketorolac | 4.0 parts. |

In accordance with this formulation, a plaster was produced by the same method as described in the above Example 1.

EXAMPLE 17

| | |
|---|---|
| Styrene/isoprene/styrene block copolymer (tradename: Cariflex TR-1107) | 28.0 parts |
| liquid paraffin | 57.5 parts |
| butylhydroxytoluene | 2.0 parts |
| rosin ester derivative (tradename: Ester Gum H) | 9.0 parts |
| l-menthol | 2.5 parts |
| ketorolac | 1.0 part. |

In accordance with this formulation, a plaster was produced by the same method as described in the above Example 1.

EXAMPLE 18

| | |
|---|---|
| Styrene/isoprene/styrene block copolymer (tradename: Cariflex TR-1112) | 21.0 parts |
| liquid paraffin | 59.0 parts |
| butylhydroxytoluene | 2.0 parts |
| rosin ester derivative (tradename: Ester Gum H) | 10.0 parts |
| l-menthol | 6.0 parts |
| ketorolac tromethamine | 2.0 parts. |

In accordance with this formulation, a plaster was produced by the same method as described in the above Example 1.

EXAMPLE 19

| | |
|---|---|
| Styrene/isoprene/styrene block copolymer (tradename: Cariflex TR-1111) | 33.0 parts |
| liquid paraffin | 58.0 parts |
| butylhydroxytoluene | 2.0 parts |
| rosin ester derivative (tradename: Foral 105) | 5.0 parts |
| l-menthol | 1.5 parts |
| ketorolac | 0.5 parts. |

In accordance with this formulation, a plaster was produced by the same method as described in the above Example 1.

EXAMPLE 20

| | |
|---|---|
| Styrene/isoprene/styrene block copolymer (tradename: Cariflex TR-1111) | 20.0 parts |
| polyisobutylene (mfd. by Exxon Co.) | 5.0 parts |
| liquid paraffin | 58.0 parts |
| butylhydroxytoluene | 2.0 parts |
| rosin ester derivative (tradename: KE-311) | 10.0 parts |
| l-menthol | 3.0 parts |
| ketoprofen | 2.0 parts. |

In accordance with this formulation, a plaster was produced by the same method as described in the above Example 1.

EXAMPLE 21

| | |
|---|---|
| Styrene/isoprene/styrene block copolymer (tradename: Cariflex TR-1111) | 15.0 parts |
| polyisobutylene (mfd. by Exxon Co.) | 14.0 parts |
| liquid paraffin | 36.0 parts |
| butylhydroxytoluene | 2.0 parts |
| rosin ester derivative (tradename: KE-311) | 25.0 parts |
| l-menthol | 5.0 parts |
| ketoprofen | 3.0 parts. |

In accordance with this formulation, a plaster was produced by the same method as described in the above Example 1.

EXAMPLE 22

| | |
|---|---|
| Styrene/isoprene/styrene block copolymer (tradename: Cariflex TR-1111) | 22.0 parts |
| polyisobutylene (mfd. by Exxon Co.) | 8.0 parts |
| liquid paraffin | 50.0 parts |
| butylhydroxytoluene | 1.0 part |
| rosin ester derivative (tradename: KE-311) | 14.0 parts |
| l-menthol | 3.0 parts |
| ketorolac | 2.0 parts. |

In accordance with this formulation, a plaster was produced by the same method as described in the above Example 1.

EXAMPLE 23

| | |
|---|---|
| Styrene/isoprene/styrene block copolymer (tradename: Cariflex TR-1111) | 15.0 parts |
| polyisobutylene (mfd. by Exxon Co.) | 12.0 parts |
| liquid paraffin | 25.0 parts |
| butylhydroxytoluene | 2.0 parts |
| rosin ester derivative (tradename: KE-311) | 38.0 parts |
| l-menthol | 4.0 parts |
| ketorolac | 4.0 parts. |

In accordance with this formulation, a plaster was produced by the same method as described in the above Example 1.

Comparative Example 1

A plaster was produced by using the same composition and the same production method as described in the above Example 4 except that no rosin ester derivative (Ester Gum H) was added.

Comparative Example 2

A plaster was produced by using the same composition and production method as described in the above Example 4 except that no l-menthol was added.

Comparative Example 3

A plaster was produced by using the same composition and production method as described in the above Example 8 except that no rosin ester derivative (KE-311) was added.

Comparative Example 4

A plaster was produced by using the same composition and production method as described in the above Example 8 except that no l-menthol was added.

Comparative Example 5

A plaster was produced by using the same composition and production method as described in the above Example 10 except that no rosin ester derivative (KE-311) was added.

Comparative Example 6

A plaster was produced by using the same composition and production method as described in the above Example 10 except that no l-menthol was added.

Comparative Example 7

A plaster was produced by using the same composition and production method as described in the above Example 17 except that no rosin ester derivative (Ester Gum H) was added.

Comparative Example 8

A plaster was produced by using the same composition and production method as described in the above Example 17 except that no l-menthol was added.

Comparative Example 9

A plaster was produced by using the same composition and production method as described in the above Example 4 except that the polyester cloth (PET cloth) employed as the backing was replaced by a polyurethane cloth.

Comparative Example 10

A plaster was produced by using the same composition and production method as described in the above Example 8 except that the polyester cloth (PET cloth) employed as the backing was replaced by a polyurethane cloth.

Comparative Example 11

A plaster was produced by using the same composition and production method as described in the above Example 10 except that the polyester cloth (PET cloth) employed as the backing was replaced by a polyurethane cloth.

Comparative Example 12

A plaster was produced by using the same composition and production method as described in the above Example 17 except that the polyester cloth (PET cloth) employed as the backing was replaced by a polyurethane cloth.

Comparative Example 13

A plaster was produced by using the same composition and production method as described in the above Example 4 except that the polyester cloth (PET cloth) employed as the backing was replaced by a PVC film.

Comparative Example 14

A plaster was produced by using the same composition and production method as described in the above Example 8 except that the polyester cloth (PET cloth) employed as the backing was replaced by a PVC film.

Comparative Example 15

A plaster was produced by using the same composition and production method as described in the above Example 10 except that the polyester cloth (PET cloth) employed as the backing was replaced by a PVC film.

Comparative Example 16

A plaster was produced by using the same composition and production method as described in the above Example 17 except that the polyester cloth (PET cloth) employed as the backing was replaced by a PVC film.

Referential Example 1

96 parts of an acrylic pressure-sensitive adhesive Nissetsu PE-300 (tradename, mfd. by Nippon Carbide Industries Co., Ltd.) were mixed with 4 parts of ketoprofen. The resulting mixture was spread on a polyester film which had been subjected to a mold-release treatment and then a polyester cloth was pressed onto the spread mixture to effect transfer of the mixture, after which the product obtained was cut into pieces of a desired size to thereby give plasters.

Referential Example 2

A plaster was produced by using the same composition and production method as described in the above Referential Example 1 except that the ketoprofen was replaced by flurbiprofen.

Referential Example 3

A plaster was produced by using the same composition and production method as described in the above Referential Example 1 except that the ketoprofen was replaced by loxoprofen.

Referential Example 4

A plaster was produced by using the same composition and production method as described in the above Referential Example 1 except that the ketoprofen was replaced by ketorolac.

Test Example 1 (Dissolution-stability test)

Using the plasters of Examples 4, 8, 10 and 17 and Comparative Examples 1 to 8, a stability test was effected by storing said plasters for one month at 5° C. Table 1 summarizes the results.

Each test sample was hermetically packed with an aluminum composite film and stored for one month at a temperature of 5° C. Then, the sealed package was opened, and the surface of the test sample was observed by using a stereoscopic microscope (Nikon Co. Ltd., magnification: ×100). When even one piece of precipitated crystal was found in the test sample, the test sample was marked by "X", whereas when the test sample was completely dissolved without generating any precipitated crystal, the test sample was marked by "O" as non-defective.

BRIEF DESCRIPTION OF THE DRAWING

FIG. 1 shows the skin penetration percent per hour of Examples 4, 8, 10 and 17 and Reference Examples 1, 2, 3 and 4.

TABLE 1

| Ex. No. | 5° C., 1 month | Conditions after the test |
| --- | --- | --- |
| Ex. 4 | O | no change |
| Ex. 8 | O | no change |
| Ex. 10 | O | no change |
| Ex. 17 | O | no change |
| Comp. Ex. 1 | X | crystallization |
| Comp. Ex. 2 | X | crystallization |
| Comp. Ex. 3 | X | crystallization |
| Comp. Ex. 4 | X | crystallization |
| Comp. Ex. 5 | X | crystallization |
| Comp. Ex. 6 | X | crystallization |
| Comp. Ex. 7 | X | crystallization |
| Comp. Ex. 8 | X | crystallization |

Test Example 2 (Drug-release test 1)

Using the plasters of Examples 4, 8, 10 and 17 and Comparative Examples 1 to 8, a test on the release of the drug into water was effected to determine the ratio of drug release-from each plaster. Table 2 summarizes the results.

TABLE 2

| Ex. No. | Drug release ratio after 4 hrs. (%) |
| --- | --- |
| Ex. 4 | 53.10 ± 2.89 |
| Ex. 8 | 46.77 ± 3.14 |
| Ex. 10 | 48.82 ± 2.55 |
| Ex. 17 | 40.92 ± 3.66 |
| Comp. Ex. 1 | 21.60 ± 1.07 |
| Comp. Ex. 2 | 27.72 ± 2.32 |
| Comp. Ex. 3 | 24.13 ± 1.98 |
| Comp. Ex. 4 | 26.95 ± 1.91 |
| Comp. Ex. 5 | 19.97 ± 1.84 |
| Comp. Ex. 6 | 25.98 ± 2.83 |
| Comp. Ex. 7 | 20.12 ± 2.80 |
| Comp. Ex. 8 | 19.92 ± 2.66 |

The results given in the above Tables 1 and 2 clearly reveal that the combined use of a rosin ester derivative with l-menthol is essential for the preparation of the plasters of the present invention.

Test Example 3 (Drug-release test 2)

Using the plasters of Comparative Examples 9 to 12, a test on the release of the drug into water was effected in the same manner as the one employed in the above Test Example 2 to determine the ratio of the drug release from each plaster. Table 3 summarizes the results. For comparison, the data for the plasters of Examples 4, 8, 10 and 17 obtained in Test Example 2 are also listed.

TABLE 3

| Ex. No. | Drug release ratio after 4 hrs. (%) |
| --- | --- |
| Ex. 4 | 53.10 ± 2.89 |
| Ex. 8 | 46.77 ± 3.14 |
| Ex. 10 | 48.82 ± 2.55 |
| Ex. 17 | 40.92 ± 3.66 |
| Comp. Ex. 9 | 15.21 ± 2.00 |
| Comp. Ex. 10 | 13.19 ± 0.98 |
| Comp. Ex. 11 | 13.57 ± 1.69 |
| Comp. Ex. 12 | 19.26 ± 2.94 |

The results given in the above Table 3 clearly show that the drug releasability is obviously improved when a polyester cloth (PET cloth) is used as the backing. When a PBT cloth is used as the polyester cloth, similar results are obtained.

Test Example 4 (Skin penetration test on hairless mice)

Using the plasters of Examples 4, 8, 10 and 17 and Referential Examples 1 to 4, a skin penetration test on hairless mice was effected. FIG. 1 shows the results.

As FIG. 1 shows, the plasters of Examples 4, 8, 10 and 17 are obviously superior to those of Referential Examples 1 to 4 in drug release ratio and bioavailability (skin penetration ratio).

Test Example 5 (Sticking test)

The plasters of Example 4 and Comparative Example 13 were stuck to the elbows of 30 healthy male human subjects for 8 hours. Table 4 shows the results.

TABLE 4

| Ex. No. | Stickiness | Fitness feeling |
| --- | --- | --- |
| Ex. 4 | ◯ | ◯ |
| Comp. Ex. 13 | X | X |

◯: good, X: poor,

Also, the plasters of Examples 8, 10 and 17 and Comparative Examples 14 to 16 were tested in the same manner as above. Consequently, the results achieved by using the plasters of Examples 8, 10 and 17 were almost the same as that of Example 4, while the results of the plasters of Comparative Examples 14 to 16 were also the same as that of Comparative Example 13.

Test Example 6 (Skin safety test)

The plasters of Examples 2 and 4, Comparative Example 10 and Referential Example 1 and an adhesive plaster of The Pharmacopoeia of Japan were stuck to the upper dorsal parts of 30 healthy male human subjects for 8 hours per day for 7 days. Table 5 summarizes the results. The post-test conditions were evaluated according to the following criteria:

±: slight rubefaction,
+: obvious rubefaction,
++: severe rash.

TABLE 5

| | No. of subjects | | | Positive ratio (%) | |
| --- | --- | --- | --- | --- | --- |
| Ex. No. | ++ | + | ± | + or above | ± or above |
| Ex. 2 | 0 | 0 | 1 | 0 | 3.3 |
| Ex. 4 | 0 | 0 | 2 | 0 | 6.7 |
| Comp. Ex. 10 | 0 | 2 | 3 | 6.7 | 16.7 |
| Ref. Ex. 1 | 1 | 3 | 6 | 13.3 | 33.3 |
| Adhesive plaster of Japan | 2 | 4 | 6 | 20.0 | 40.0 |

As the results given in the above Tables 4 and 5 clearly show that the antiphlogistic analgesic plaster of the present invention is a product which is excellent in convenient use thereof and is very safe.

INDUSTRIAL APPLICABILITY

As described above, the solubility and release characteristics of a nonsteroidal antiphlogistic analgesic drug are enhanced by the practice of the present invention, thereby to make it possible to achieve a high drug efficacy and furthermore to remarkably relieve skin rash. Thus, the antiphlogistic analgesic plaster of the present invention is one which can also be conveniently used and is highly useful in the industrial field.

We claim:

1. An antiphlogistic analgesic plaster consisting essentially of:
   (a) a nonsteroidal antiphlogistic analgesic drug selected from the group consisting of ketoprofen, flurbiprofen, loxoprofen, ketorolac, ester derivatives salts thereof, and mixtures thereof;
   (b) a solubilizer comprising a combination of a rosin ester derivative with l-menthol;
   (c) a styrene/isoprene/styrene block copolymer employed as a base polymer;
   (d) a softener selected from the group consisting of oils, olefinic acids, and liquid paraffin; and
   (e) a backing comprising a polyester cloth, the nonsteroidal antiphlogistic analgesic drug, rosin ester derivative, l-menthol, styrene/isoprene/styrene block copolymer and softener being present in respective mixing ratios by weight of from 0.5 to 10.0%, from 5.0 to 70.0%, from 0.5 to 15.0%, from 5.0 to 40.0% and from 10.0 to 75.0% in this order, the amounts of all said ingredients totalling 100% by weight,
   the nonsteroidal antiphlogistic analgesic drug, rosin ester derivative and l-menthol being present in a mixing ratio of 1.0:3.0–11.0:1.0–4.0.

2. The plaster according to claim 1 which contains 7 parts of said rosin ester derivative, 3 parts of l-menthol and 1 part of ketoprofen.

3. The plaster according to claim 1 which contains 8 parts of said rosin ester derivative, 1.2 parts of l-menthol and 1 part of flurbiprofen.

4. The plaster according to claim 1 which contains 8 parts of said rosin ester derivative, 3 parts of l-menthol and 1 part of loxoprofen.

5. The plaster according to claim 1 which contains 9 parts of said rosin ester derivative, 2.5 parts of l-menthol and 1 part of ketorolac.

* * * * *